United States Patent [19]

Privas

[11] 3,971,229
[45] July 27, 1976

[54] APPARATUS FOR PRODUCING COLD PRINCIPALLY FOR THE APPLICATION OF COLD BY CONTACT ON THE BODY OF LIVING BEINGS

[75] Inventor: Yves Emile Privas, Killowen-Blarney, Ireland

[73] Assignee: Panoduz-Anstalt Co., Vadu, Liechtenstein

[22] Filed: Mar. 20, 1973

[21] Appl. No.: 342,962

[30] Foreign Application Priority Data
Mar. 29, 1972 Switzerland.................... 554,683
Nov. 22, 1972 Switzerland.................... 574,259

[52] U.S. Cl. ..................................................... 62/3
[51] Int. Cl.² ...................................... F25B 21/02
[58] Field of Search ................ 62/3; 128/399, 303.1

[56] References Cited
UNITED STATES PATENTS

| | | | |
|---|---|---|---|
| 413,136 | 10/1889 | Dewey | 62/3 |
| 2,798,493 | 7/1957 | Sukacev | 62/3 |
| 2,798,494 | 7/1957 | Sukacev | 62/3 |
| 2,938,356 | 5/1960 | McMahon | 62/3 |
| 3,088,288 | 5/1963 | Elfving | 62/3 |
| 3,093,135 | 6/1973 | Hirschhorn | 62/3 |
| 3,130,553 | 4/1964 | Makow | 62/3 |
| 3,133,539 | 5/1964 | Eidus | 62/3 |
| 3,146,600 | 9/1964 | Cop | 62/3 |
| 3,200,601 | 8/1965 | Bird | 62/3 |
| 3,207,159 | 9/1965 | Tateisi | 62/3 |
| 3,274,995 | 9/1966 | Eidus | 62/3 |
| 3,369,549 | 2/1968 | Armao | 62/3 |
| 3,502,080 | 3/1970 | Hirschhorn | 62/3 |
| 3,713,302 | 1/1973 | Reviel | 62/3 |

OTHER PUBLICATIONS

"Thermoelectric Refrigeration" by J. Kelly pp. 89, 90 and 91 in Air Conditioning, Heating and Ventilating, Mar. 1959.

*Primary Examiner*—Lloyd L. King

[57] ABSTRACT

Apparatus for generating cold, principally for the application of cold by contact on the body of living beings, constituted by a very small, light apparatus which is easy to take hold of and easy to handle in one hand, comprising a body carrying a very small generator rapidly generating cold within the temperature range of −10°C to −80°C, the surface of application of cold by contact being constituted by the actual surface of the generating element or by an auxiliary surface which is thermally connected to the latter.

7 Claims, 15 Drawing Figures

APPARATUS FOR PRODUCING COLD PRINCIPALLY FOR THE APPLICATION OF COLD BY CONTACT ON THE BODY OF LIVING BEINGS

An object of the present invention is to provide means affording a practical development of applications of cold, principally during a relatively short period on relatively small areas, above all in the field of contact of cold with the body of living beings and the physiological effects thus produced, for many purposes some of which are known and others to be discovered by the utilization of said means.

Within this general framework, an object of the invention is more particularly to provide means for a localized application of cold by contact which is precise as to both the point of application and the degree of cold, the duration of the application and the pressure exerted on the skin being variable in accordance with requirements without this modifying in any way the aforementioned precision.

A further object of the invention is to provide means for effecting an alternating application of cold and hot with the same apparatus.

At the present time, for the use of cold in the field in question, there is available practically only ice for moderate colds and carbonic acid snow for extreme colds of the order of −80°C. The use of carbonic acid is impossible for the application of moderate colds and the use of ice hardly permits descending below −20°C so that, between −20°C and −100°C, the use of cold in the field in question is practically non existent for want of suitable means. Another object of the present invention is to satisfy this need by providing means for regulating as desired the degree of the cold applied within the temperature range of 0° to −80°C. Moreover, ice taken below 0°C rapidly heats up at the point of application so that the degree of cold applied varies rapidly and in an uncontrollable manner in the course of an application and this has a distinctly adverse effect on the expected physiological results.

An object of the invention is therefore to provide means for employing a degree of cold which is substantially permanent during the application, it being preferably possible to control this degree during the application so as to maintain it constant or, on the contrary, to control the variation.

Further, ice is hardly practical to employ. In particular, with ice, it is difficult to achieve a precise localization of a small point of application of the order of a few square centimetres. Moreover, ice does not ensure the desirable asepsis owing to the immediate melting of the applied surface.

As concerns carbonic acid snow, it can only be employed at a fixed station since it requires complex, heavy and large units which are costly and expensive to employ and can only be used by specialists.

The problem set by this present state of affairs is solved by the present invention by the provision of the new industrial product constituted by a very small, light apparatus which is easy to take hole of and handle with one hand, has approximately the size of an electric razor, is of utility for private individual use and professional use and comprises a body carrying a small generator of cold within the temperature range of −10°C to −80°C, the surface of application of the cold by contact being constituted by the actual surface of the generating element or by an auxiliary surface thermally connected to the latter.

In a preferred embodiment of such an apparatus, the generator comprises at least one thermoelement having a Peltier effect and the apparatus also carries means for cooling the hot face of the thermoelement and means for supplying electric current to the generating element including means for connecting and disconnecting said supply of current.

An apparatus arranged in this way completely solves the problem which is with another cold generator solved only in its general aspect of development of applications of cold by contact but not in all its particular aspects.

In one embodiment of such an apparatus, the body is hollow and encloses said cooling means and the means for supplying electric current to the generating element.

In order to render the apparatus completely independent, the current supply means are advantageously constituted by a rechargeable small dry battery of small capacity. The apparatus is then completed by an electric plug carried by the body for directly connecting to a charger.

For apparatuses intended for intermittent operation of short duration for each utilization, the means for cooling the hot face of the generating element are preferably constituted by a simple mass of a metal which is a good thermal conductor known per se to which one face of the thermoelement is welded or soldered.

In the particular case of an apparatus intended for medical use requiring high precision in the application of cold, in particular as concerns the degree of the cold, the apparatus carries means welded or soldered to the cold face of the cold generator for association with a thermal probe, these means being constituted for example by a wire of such a probe or connecting means for such a wire.

If it is desired that the apparatus also permits alternating applications of cold and hot, the body of the apparatus carries means for reversing the current supply of the cold generating element, these means comprising two circuits which are connected to a reversing switch, or each circuit includes its own push-button having a switch-opening spring.

The new product constituted by the apparatus thus completely solves the problem owing to the fact that it is light, small, cheap, easy to handle, and can be employed by any one in any circumstances and it permits achieving the known physiological effects of cold in many cases where this possibility of utilization did not exist. Thus it constitutes a means for employing cold in cases in respect of which no means existed and a means of research and testing of new therapeutic applications of cold. In addition to its use in medical, surgical or dental therapeutics by qualified practictioners, there may be mentioned among other uses its use as an essential product in first aid outfit the possibility of employing it at home, in the open air, when camping, on building sites, on the road, on a boat, and in any sick-room of communities, schools, factories etc.

It is also possible to employ the basic elements of the apparatus for constituting the source of cold of a toy in the form of a miniature refrigerator. Further, the heat liberated may be advantageously employed for supplying heat to a cooking hot plate. In this way there is afforded an apparatus generating cold housed within a case provided with at least one access door and the usual accessories of a refrigerator and supplied with power by an electric battery provided with a switch.

Advantageously, it is disposed in the upper part of the case and at least one thermoconductive plate is disposed in contact with its radiator. The case may be provided with means for access through its top side and include at least one aperture for the passage of a thermoconductive plate.

In the figures of the accompanying drawing, given solely by way of non-limitative examples.

In the embodiment shown in FIGS. 1–5, the apparatus comprises a tubular cylindrical body 1 closed at one end by a plug 2 provided with a peripheral groove 3 in which a sealing element 4 is disposed and a flange 5 which bears against the end of the tube 1. Disposed in the part adjacent the exterior of the body 1 is a battery 6 whose terminals are connected to two wires 7, 8. In one of the wires there is inserted a switch 9 having a push-button 10 which is in alignment with an aperture in the body 1 so as to permit depressing the push-button from the exterior of the apparatus.

Figure 1:
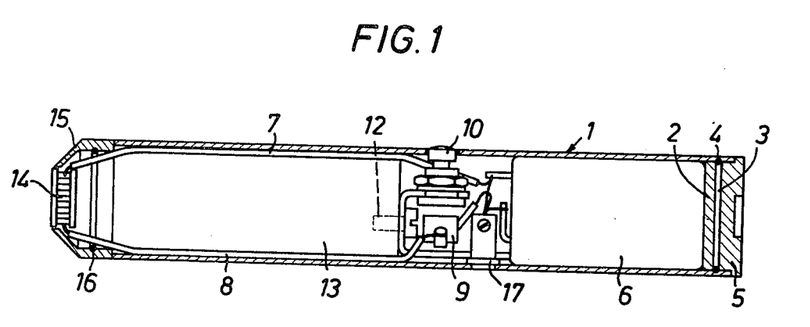
FIG. 1 shows, substantially to scale, an axial sectional view of one embodiment of the apparatus according to the invention.
Figure 2:
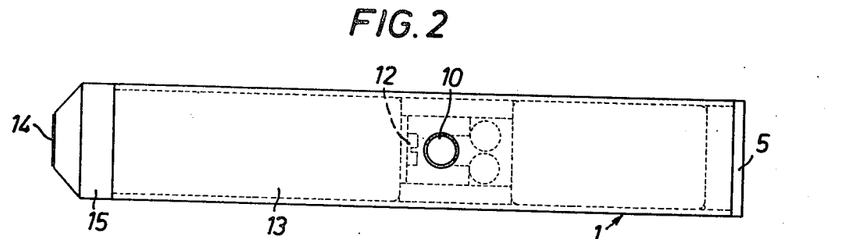
FIG. 2 is an elevational view of the apparatus.
Figure 3:
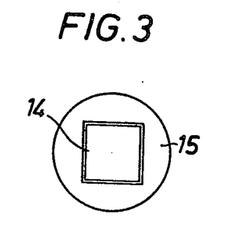
FIG. 3 is an end elevational view in the direction of arrow F.
Figure 4:
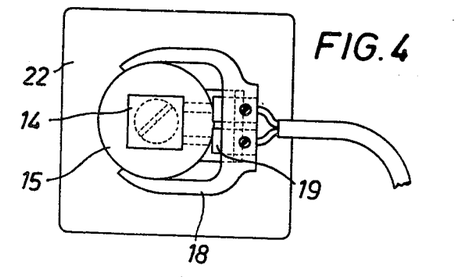
FIG. 4 is a view of a support for the apparatus shown in FIG. 1 for recharging the apparatus.
Figure 5:
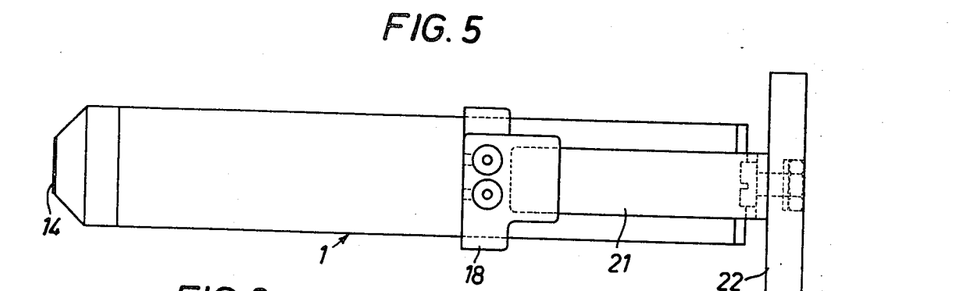
FIG. 5 is a view of the support combined with the apparatus.

The switch 9 is secured by a screw 12 to the end of a cylindrical metal mass 13, preferably of aluminium, which occupies the whole of the remaining part of the tube 1 and is provided with two longitudinal recesses affording a passage for the wires 7 and 8. Welded or soldered to the end of the mass 13 is a small thermoelement 14 having a Peltier effect, of known type to which the wires 7 and 8 are connected. The cold face of the thermoelement 14 constitutes the actual surface of application of cold.

The thermal mass 13 extends beyond the end of the remaining part of the body 1 and fitted on this projecting part, which has a slightly smaller diameter, is a cap 15 which an internal ring 16 maintains on the mass 13 and which is provided with a centre aperture through which the thermal-element 14 slightly projects to the exterior by its cold face.

For the purpose of recharging the battery 6, there are provided two terminals 17 for receiving current which are disposed inside the body 1 between the switch 9 and the battery 6 in alignment with two apertures in the tube 1. A resiliently-yieldable clip 18 is also associated with the apparatus (FIG. 4), the clip having branches capable of surrounding the apparatus and the clip having between these branches pins 19 connected by a cable 20 to a charger (not shown). These pins 19 fit into the terminals 17 of the apparatus when the latter is inserted in the clip 18 which also serves as a support for the apparatus since it is integral with an arm 21 and a base 22.

Figure 6:
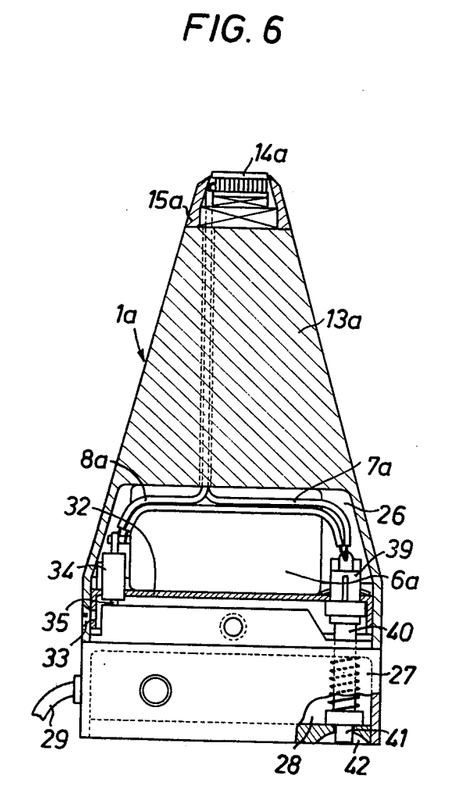
FIG. 6 is a sectional view of another embodiment of the apparatus according to the invention.
Figure 7:
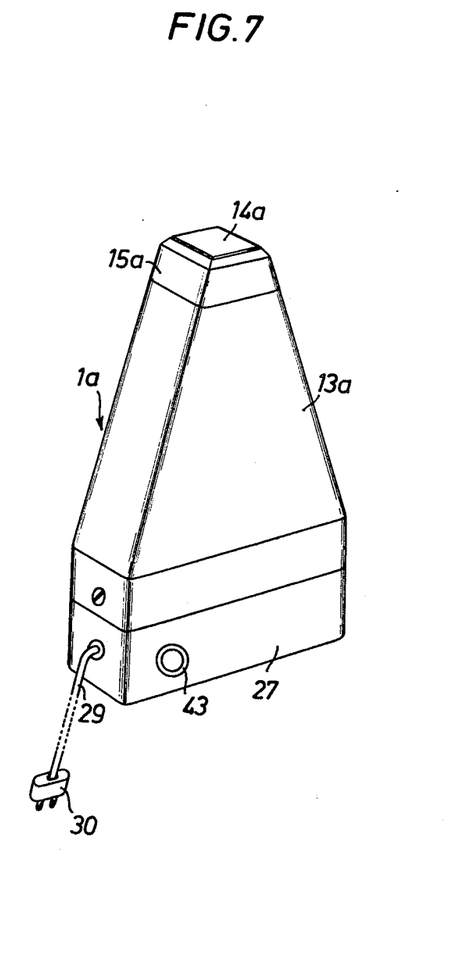
FIG. 7 is a perspective view of the apparatus shown in FIG. 6.

In the embodiment shown in FIGS. 6 and 7, it is the thermal mass 13a which constitutes the actual body of the apparatus the general shape of which is defined by two substantially parallel plane faces, each being in the form of an isosceles trapezium. This mass is hollowed out at 26 in the widest part of the mass so as to accomodate therein the battery 6a which is here parallel to the cold face of the thermoelement 14a, which face is welded or soldered, as in FIG. 1, to the end of the thermal mass which is shaped to receive a cap 15a of plastics material. The cap 15a surrounds the thermoelement connected to the battery by the wires 7a and 8a. The end of the body opposed to that adjacent the thermoelement 14a is arranged to be placed on a base 27 which encloses a charger 28 projecting therefrom. A cable 29 and a plug 30 (FIG. 7) connect the charger to an electric mains. The projecting part of charger 28 fits in the hollow end of the thermal mass 13a which maintains the base and the charger in a fixed relative position. A cross-member 32 having L-shaped edge portions is fixed by the latter to the wall of the hollow 26 by screws 33 which extend therethrough and the battery 6a bears on these screws. It also carries a double pole current socket 34 to which the wires 7a – 8a are connected and which fits on two pins 35 of the charger. The switch 9a to which the wires 7a – 8a are connected is also carried by the member 32 through which it extends and its control button 40 is in alignment with an auxiliary button 41 which has a spring and is disposed in the base 28 and projects from the latter in a small cup-shaped recess 42 in the bottom face of the base. This auxiliary button is of utility when it is desired to handle the apparatus while it is left integral with the base 28, for example for applications of cold which are rather long or too frequent and would be liable to run down the battery, the latter being in position for charging due to the fact that it is fitted on the base. An indicator lamp 43 carried by the base serves to indicate the charging.

Figure 8:
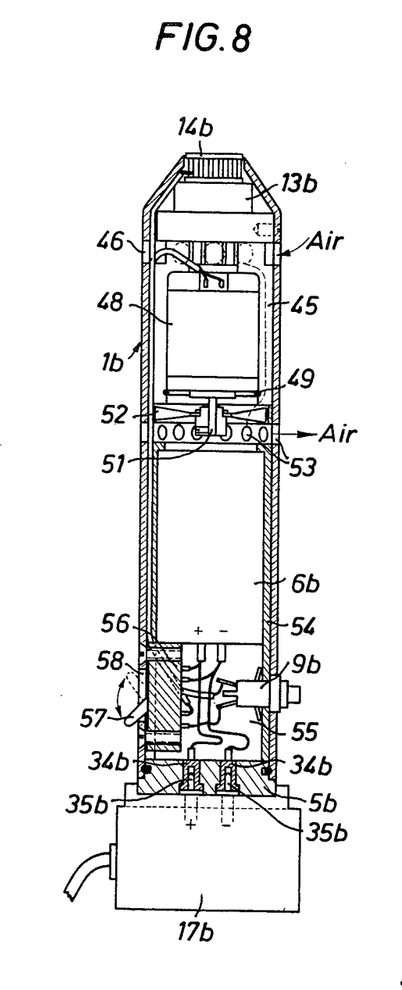
FIG. 8 is an axial sectional view of a modification of the apparatus shown in FIG. 1.
Figure 9:
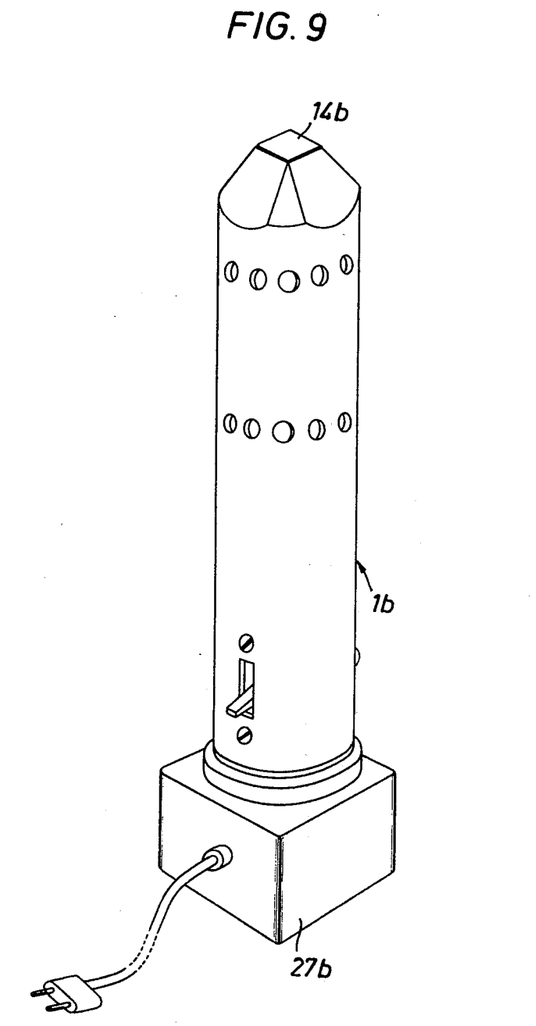
FIG. 9 is a perspective view of the modification shown in FIG. 8.

The apparatus shown in FIGS. 8 and 9 is similar to the foregoing apparatus in its general arrangement and comprises a body 1b resting on a stand 27b which is arranged in a similar way to the stand 27, but the body 1b is cylindrical and arranged on the whole in the same way as the body shown in FIG. 1 but differs from this body by the means for cooling the hot face of the thermoelement 14b. These means comprise a very small cooling mass 13b the part of which to which the thermoelement is welded or soldered is a massive part fixed by a screw to the body 1b whereas the other part is formed by a ring arrangement of radial fins 45 which is located in alignment with a ring arrangement of orifices 46 formed in the tube 1b. These fins extend longitudinally of the tube 1b around a motor 48 whose axis coincides with the axis of the tube, the motor being centered by the fins. The motor is held in position in the longitudinal direction by a ring 49 placed at one of its ends whereas the other end of the motor is applied against the finned face of the cooling mass 13b. The shaft 51 of the motor is at the first of these ends and carries fan means 52, the periphery of which is in alignment with the fins 45, between their ends and a ring arrangement of orifices 53 which extend through the wall of the body 1. On the other side of the ring arrangement of orifices 53, there is disposed the battery 6b centered in a sleeve 54 which is mounted in the body 1b and extends to the end of the latter, this end being closed by a plug 5b as in the arrangement shown in FIG. 1. It is through this end that the body 1b rests on the base 17b (which is similar to the base 17 shown in FIGS. 5 and 6) in the upper part of which base it is inserted. The connections 34b, 35b between the charger enclosed in the base and the means to be supplied with current are by way of the plug 5b, the sockets 34b being carried by the plug and the pins 35b by the charger. The button 9b of the switch is disposed in the space 55 between the battery 6b and the plug 5b and it extends through the walls of the sleeve 54 and tube 1b from which latter it outwardly projects a good distance. Disposed in the space 55 is also a current reversing switch 56 through which the thermoelement 14b is supplied with current. The outer face of the latter can thus be rendered cold or hot by reversing its operation. This reversing switch 56 is actuable by a lever 57 which extends out of the body 1b by way of an opening 58 in the latter.

The end of the body of the apparatus adjacent the cold-applying surface 14b is in the shape of pyramid whose truncated apices well expose this surface.

Figure 10:
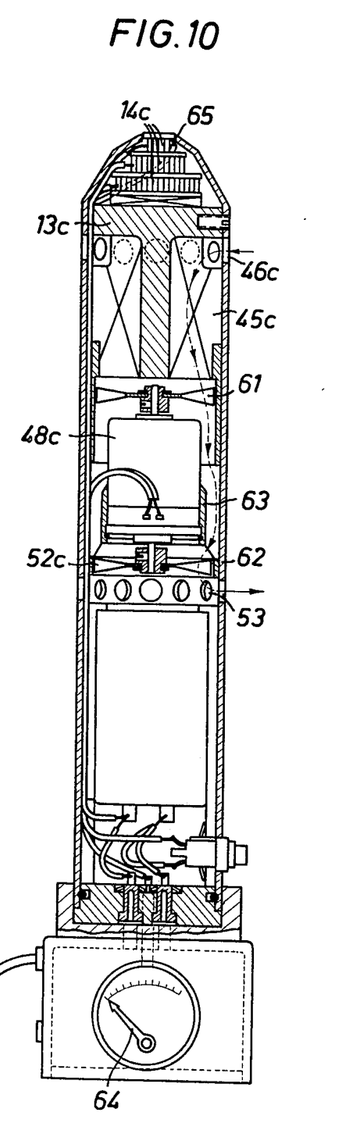
FIG. 10 is a sectional view similar to FIG. 8 of another modification.
Figure 11:
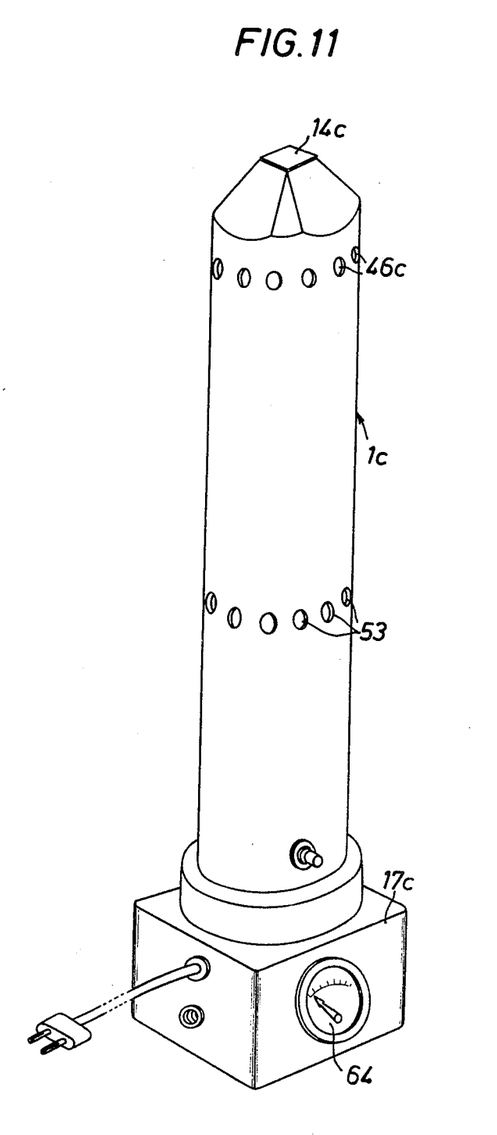
FIG. 11 is a perspective view of the modification shown in FIG. 10.

In FIGS. 10 and 11, the illustrated apparatus differs from the preceding apparatus in that the cold generating element 14c comprises a cascade arrangement of four thermoelements, the smallest of which is a square having a 5 mm side dimension and constitutes the surface of application of cold of the order of −80°C. The fins 45c of the cooling mass 13c are larger and fan means 61 are disposed between the end of the fins 45c and the motor 48c which has two shaft ends. One of the shaft ends drives the fan means 61 and the other shaft end drives another fan means 52c located, as the means shown in FIG. 8, between the motor and a ring arrangement of air outlet orifices 53c. These two fan means 52c and 61 are arranged in series so as to draw in air through a ring arrangement of orifices 46c and expel it by way of the orifices 53. The motor 48c is here centered by a sleeve 62 which comprises a skirt portion 63 centered in the body 1b and a centre hub connected to the skirt portion 63 by arms so as to allow through the air blown by the fan means 61. The motor is disposed in the sleeve 62 and maintained in axial abutment with a shoulder of the hub by a ring.

The illustrated apparatus has no reversing switch but it may include one in the same way as the apparatus described in FIGS. 8 and 9. The end of the apparatus other than that adjacent the thermoelement 14c is arranged as shown in FIG. 8 and the base 17c is provided with a temperature indicator 64 employing a thermocouple 65 fixed to the cold-applying surface.

Figures 12, 13, 14:
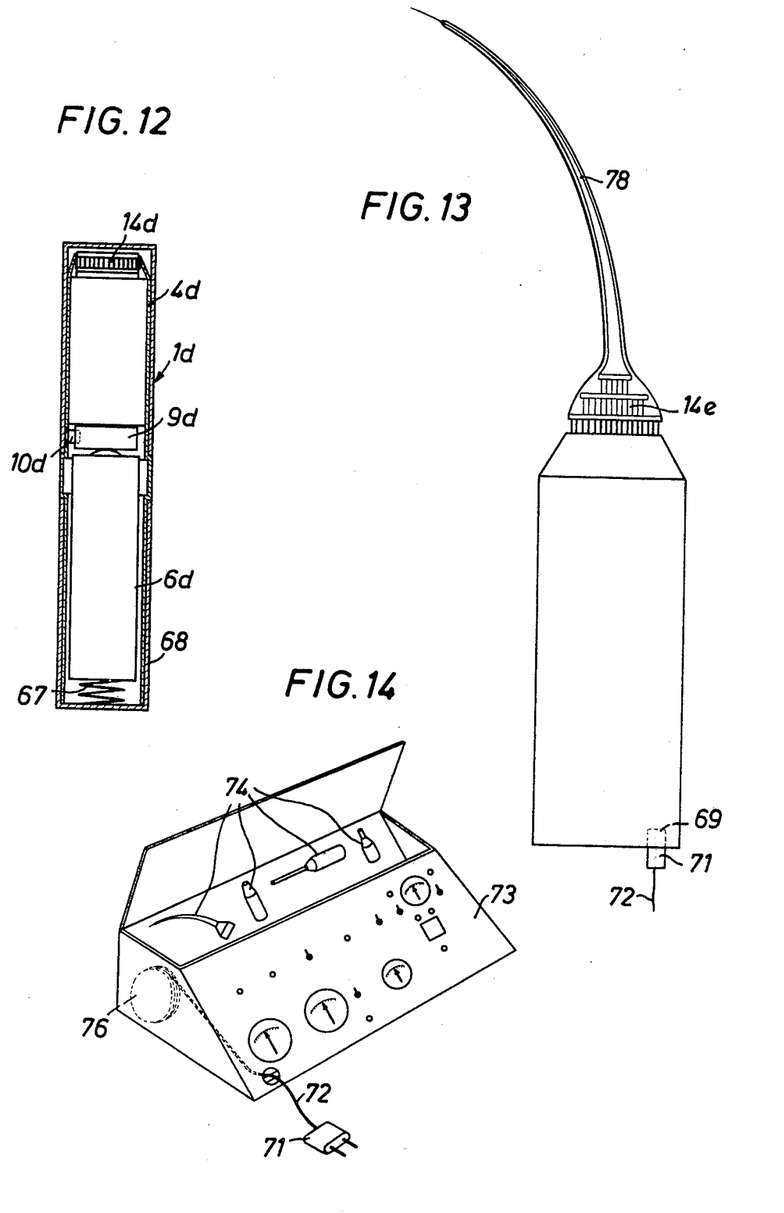
FIG. 12 is a diagrammatic sectional view of a modification of the apparatus shown in FIG. 1.
FIG. 13 is an elevational view of a modification of the apparatus shown in FIGS. 10 and 11 intended to be employed in the equipment shown in FIG. 14.
FIG. 14 is a view of an auxiliary apparatus employing the basic elements according to the invention.

In FIG. 12, reference numeral 14d represents the cold generating element of the apparatus whose arrangement is on the whole similar to that of the apparatus shown in FIG. 1, the switch here being designated by reference numeral 9d and its actuating button by 10d. The differences reside in the fact that the rechargeable battery 6 is replaced by a dry battery 6d which a spring 67 disposed between the battery and the end wall of the body 4d, urges against a contact carried by the switch block 9d. The whole of the body 4d is mounted and enclosed in a sleeve or case 68 which is similar to those of lipstick holders and preferably has a decorative character, the part which caps the generating element 14d constituting a cap which is detachable by sliding along the body 10d so that when it is mounted on the body it depresses the button 10d of the switch 9d and opens the latter and thus opens the circuit of the cold generating element 14d and maintains it in this state until the cap is removed for utilizing the cold which is developed within a few seconds by the element 14d the supply circuit of which is automatically closed by the removal of this cap.

The apparatus shown in FIG. 13 comprises the upper part of the apparatus shown in FIG. 10 cut off above the air outlet orifices 53, which part is closed by a grill (not shown) for the outlet of the air delivered by the fan means 52c. The means which carry the apparatus for supplying current to the cold generating element 14c are then limited to a current supply terminal 69 which is adapted to receive a current plug 71 to which a wire 72 is connected. This apparatus, which is in principle of rather high cold producing power is more particularly intended for professional use by qualified practictioners and this is why it is employed with an auxiliary apparatus (FIG. 14) constituted by a cabinet 73 enclosing a battery-rectifier, a switch for reversing the current supplied to the cold generating element so as to cause the latter to produce, at will, hot or cold, a variometer, a probe for measuring the temperature of the skin and various measuring and inspection apparatuses and light indicators. It also encloses a number of apparatuses 74, such as that shown in FIG. 13, intended to be selectively connected to a current supply plug 71 having pins, the wire 72 of which is connected to the battery inside the cabinet by passing around a winder 76 carried by the latter.

The cold-applying surfaces of the various apparatuses 73 differ as to the surface and shape so as to permit the practictioners to carry out various treatments.

The apparatus shown in FIG. 13 is, for example, for the application of a very localized cold of the order of −80°C in dermatology. On the smallest of the thermoelements arranged in the manner of a cascade of the cold generating element 14c there is welded or soldered a long metal needle 78 which is advantageously of silver and has a decreasing section terminating in a thin or pointed part which extends out of the end of a fluidtight glass case 78 in which a vacuum is produced. The case 78 is welded at its base in a fluidtight manner to the periphery of the largest of the thermoelements and surrounds the needle 78 at a distance therefrom so as to insulate it thermally.

Figure 15:
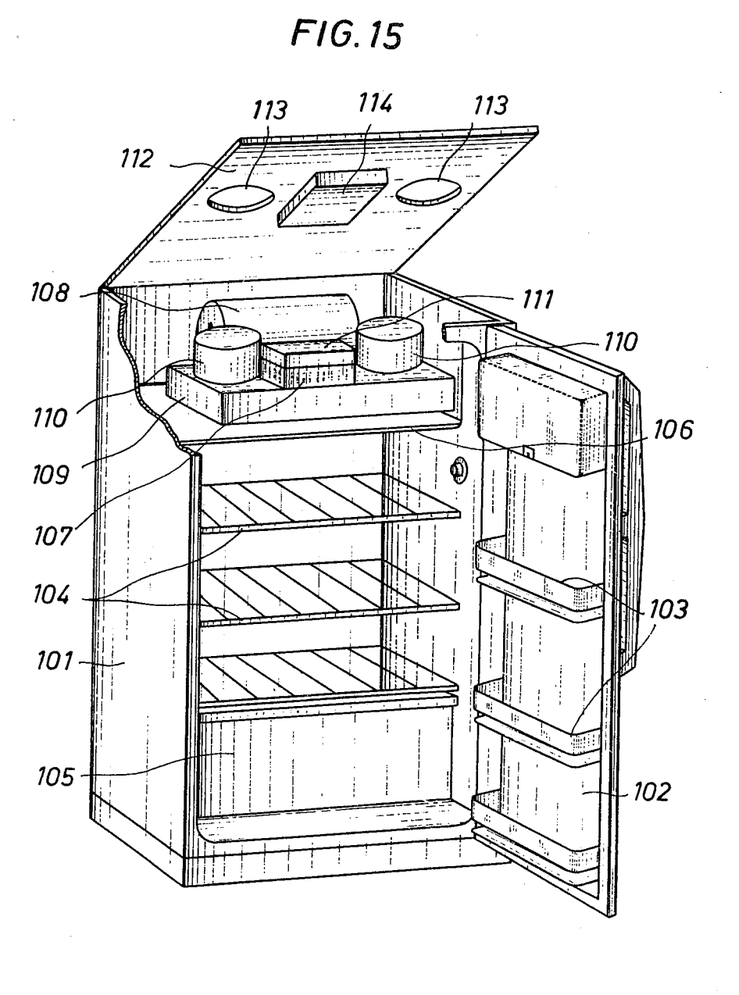
FIG. 15 is a diagrammatic perspective view, with a part cut away, of a miniature refrigerator employing the basic elements of the apparatus according to the invention.

The apparatus shown in FIG. 15 comprises a rectangular-sided case 101, for example of moulded plastics material, provided with a front door 102 equipped with receptacles 103 for bottles or the like. Mounted inside the case 101 are racks 104 and a vegetable tray 105. Disposed in the upper part of the case 101 and carried by a plate 106 are a thermoelement 107 fed with current by an electric battery 108, the radiator 109 of the thermoelement 107 comprising a lower plate surmounted by two cylindrical projecting portions 110 performing the function of hot plates. Disposed between the cylindrical projecting portions 110 and in contact with the thermoelement 107 is a tray 111 performing the function of an ice tray. The upper face of the case 101 comprises a pivoted lid 112 provided with two circular apertures 113 through which, when the lid 112 is closed, the cylindrical projecting portions 110 of the radiator 109 extend. Between the apertures 113 the interior of the lid 112 carries an insulating plate 114 adapted to be in facing relation to the ice tray 111 when the lid is closed.

The assembly just described constitutes a very attractive toy which produces simultaneously cold inside the case and gives off heat through the hot plates. A switch (not shown) closes the circuit of the thermoelement 107 and battery 108.

What I claim is:

1. An apparatus for generating cold, principally for the application of cold by contact on the body of living beings, constituted by a very small, light apparatus which is easy to take hold of and easy to handle in one hand, comprising a body carrying a very small generator rapidly generating cold within the temperature range of −10°C to −80°C, the surface of application of cold by contact being constituted by the actual surface of the generating element or by an auxiliary surface which is thermally connected to the latter, the cold generating element comprising at least one thermoelement having a Peltier effect and the apparatus also carries means for cooling the hot face of the thermoelement and means for supplying electric current to the generating element including means for connecting and disconnecting said supply of current said apparatus further including a device which acts as a support for the apparatus and which ensures the recharging of the battery through a circuit which is closed by the mere fact that the apparatus is mounted on the support.

2. An apparatus for generating cold, principally for the application of cold by contact on the body of living beings, constituted by a very small, light apparatus which is easy to take hold of and easy to handle in one hand, comprising a body carrying a very small generator rapidly generating cold within the temperature range of −10°C to −80°C, the surface of application of cold by contact being constituted by the actual surface of the generating element or by an auxiliary surface which is thermally connected to the latter, said apparatus being disposed inside a case provided with at least one access door and supplied with current by an electric battery provided with a switch, the cold generating element being disposed in the upper part of the case, and at least one thermoconductive plate being disposed in contact with the radiator of the cold generating element, said case being provided with a lid pivoted to the upper part of the case for pivotal movement between a raised position and a closed position, said lid being apertured in such a manner than when said lid is closed, the thermoconductive plate or plates extend through the apertures.

3. Apparatus for generating cold comprising a body carrying a Peltier thermoelement having a cold face and a hot face, said thermoelement being disposed inside a case provided with at least one access door and accessories usual in a refrigerator and supplied with current from an electric battery provided with a switch, said thermoelement being disposed in the upper part of said case with at least one thermally conductive plate being disposed in contact with the hot face of said element, and said case being provided with a lid pivoted to the upper part of said case for pivotal movement between a raised position and a closed position, said lid being apertured in such a manner that, when said lid is closed, said thermally conductive plate extends through said aperture, said cold face of said Peltier element being thermally connected to said case for cooling the interior of said case.

4. An apparatus for generating cold, principally for the application of cold by contact on the body of living beings, comprising a body carrying a Peltier thermoelement having a cold face with a cold surface and a hot face, said Peltier element being mounted along the periphery of said body so that said cold surface of said Peltier element is spaced outwardly of all other parts of said body and is directly engageable with the body of the living being to thus apply cold directly thereto, and means for cooling said hot face comprising an air passage having an air inlet opening and an air outlet opening in said body, said passage being in communication with said hot face of said Peltier element, and fan means for moving air through said passage to cool said hot face of said Peltier element.

5. The apparatus of claim 4 wherein said body of said apparatus comprises a plurality of external surfaces joined together along their contiguous side edges and each terminating at a free edge portion, a plurality of said free edge portions defining an opening in said body, said Peltier element being positioned in said opening with said cold surface spaced outwardly from a plane through said free edge portions.

6. The apparatus of claim 5 wherein said external surfaces define a generally quadratic shape, and wherein said opening is at a corner of said quadratic shape, a plane through said free edge portions being at an angle to all of said surfaces.

7. The apparatus of claim 6 wherein said cold surface is substantially planar, and is at an angle to all of said external surfaces.

* * * * *